(12) United States Patent
Nabeshima et al.

(10) Patent No.: US 8,827,928 B2
(45) Date of Patent: Sep. 9, 2014

(54) GUIDE WIRE

(75) Inventors: Yousuke Nabeshima, Shizuoka (JP);
Noriyuki Tamai, Shizuoka (JP); Yutaka Tano, Shizuoka (JP); Ryuuichi Watanabe, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/613,470

(22) Filed: Sep. 13, 2012

(65) Prior Publication Data
US 2013/0006222 A1    Jan. 3, 2013

Related U.S. Application Data

(63) Continuation of application No. PCT/JP2011/056015, filed on Mar. 15, 2011.

(30) Foreign Application Priority Data

Mar. 26, 2010   (JP) ................................. 2010-073426

(51) Int. Cl.
*A61M 25/00* (2006.01)
*A61M 25/09* (2006.01)

(52) U.S. Cl.
CPC .................................... *A61M 25/09* (2013.01)
USPC ...................................................... 600/585

(58) Field of Classification Search
CPC .......... A61B 5/6851; A61M 25/09016; A61M 25/09025; A61M 25/09033; A61M 25/09041; A61M 25/0905; A61M 1/00
USPC .......................................... 600/585; 604/523
See application file for complete search history.

(56) References Cited

U.S. PATENT DOCUMENTS 7,753,859 B2 *    7/2010   Kinoshita et al. ............. 600/585
8,052,620 B2 *   11/2011   Ishida et al. .................. 600/585
(Continued)

FOREIGN PATENT DOCUMENTS

EP    0 838 230 A2    4/1998
EP    2 014 329 A1    1/2009
(Continued)

OTHER PUBLICATIONS

International Search Report (PCT/ISA/210) issued on May 10, 2011, by the Japanese Patent Office as the International Searching Authority for International Application No. PCT/JP2011/056015.
(Continued)

*Primary Examiner* — Adam Eiseman
(74) *Attorney, Agent, or Firm* — Buchanan Ingersoll & Rooney PC (57) ABSTRACT

A guide wire includes: a flexible elongate wire body; and a coating layer that covers a distal portion of the wire body and is formed of a resin material. The wire body of the guide wire is provided with a projection that protrudes along the entire circumference of an outer circumferential portion of the wire body. A distal portion of the projection is in contact with a proximal portion of the coating layer, and the maximum outside diameter of the projection is larger than the outside diameter of the coating layer that is in contact with the projection. In addition, a proximal portion of the projection has an outside diameter tapering portion where the outside diameter is gradually reduced toward a proximal end.

18 Claims, 7 Drawing Sheets

(56) References Cited

U.S. PATENT DOCUMENTS

| | | |
|---|---|---|
| 2003/0225418 A1 | 12/2003 | Esksuri et al. |
| 2003/0229298 A1* | 12/2003 | Iwami et al. ............... 600/585 |
| 2004/0039308 A1* | 2/2004 | Murayama et al. .......... 600/585 |
| 2008/0281230 A1* | 11/2008 | Kinoshita et al. ............ 600/585 |
| 2008/0306468 A1 | 12/2008 | Tamai et al. |

FOREIGN PATENT DOCUMENTS

| | | |
|---|---|---|
| JP | 2004-16359 A | 1/2004 |
| JP | 2005-527332 A | 9/2005 |
| JP | 2008-307367 A | 12/2008 |
| JP | 2009-160121 A | 7/2009 |
| WO | WO 2007/105531 A1 | 9/2007 |
| WO | 2008/100877 A2 | 8/2008 |

OTHER PUBLICATIONS

European Search Report dated Sep. 4, 2013, issued by the European Patent Office in corresponding European Patent Application No. 11759249.3. (5 pages).

Chinese Office Action dated Jan. 8, 2014, issued by the Chinese Patent Office in corresponding Chinese Patent Application No. 201180015394.2. (6 pages).

* cited by examiner

FIG. 7 dd# GUIDE WIRE

CROSS REFERENCES TO RELATED APPLICATIONS

This application is a continuation of International Application No. PCT/JP2011/056015 filed on Mar. 15, 2011, and claims priority under 35 U.S.C. §119 to Japanese Patent Application No. 2010-073426 filed in the Japanese Patent Office on Mar. 26, 2010, the entire content of both of which is incorporated herein by reference.

TECHNICAL FIELD

The present invention relates to a guide wire.

BACKGROUND DISCUSSION

At the time of inserting a catheter into a body lumen such as a digestive tract or a blood vessel, a guide wire is used to guide the catheter to a target site in the body lumen. The guide wire is used in the state of being inserted in the catheter. In addition, observation and treatment of a body lumen or the like by use of an endoscope is also practiced. In this case, also, a guide wire is used to guide the endoscope or the catheter inserted in the lumen of the endoscope to a target site in the body lumen or the like.

A known guide wire includes a elongate wire body, a resin coating layer covering a distal portion of the wire body, and an annular member disposed on a proximal portion of the resin coating layer and with which a stepped space between the wire body and the resin coating layer is filled up. An example of this guide wire is disclosed in Japanese Patent Laid-open No. 2008-307367. The guide wire described in this document has a configuration in which an outside diameter at a proximal end of the resin coating layer and an outside diameter at a distal end of the annular member are equal, and the proximal end of the resin coating layer and the distal end of the annular member are bound to each other.

In a situation in which a distal portion of this guide wire is curved with a comparatively small radius of curvature, the proximal end of the resin coating layer and the distal end of the annular member may be separated from each other, producing a crack in the boundary between them. Specifically, the proximal portion of the resin coating layer may peel from the wire body, and may turn up. When the catheter is pushed in from a proximal end of the guide wire being in this state along the guide wire, a distal end of the catheter may be caught on the turned-up part.

SUMMARY

The guide wire includes a flexible elongate wire body, a coating layer covering a distal portion of the wire body and formed of a resin material, the coating layer possessing an outer diameter, the wire body including a projection which projects along an entire circumference of an outer circumferential portion of the wire body, with the projection possessing a distal portion in contact with a proximal portion of the coating layer, and the projection possessing a maximum outside diameter greater than the outside diameter of the proximal portion of the coating layer that is in contact with the projection.

In accordance with another aspect, the guide wire includes a flexible elongate solid wire body possessing a distal portion terminating at a distal-most end and a proximal portion terminating at a proximal-most end, a projection fixed to the wire body, and a coating layer fixed to and covering at least a part of the distal portion of the wire body. At least a part of the distal portion of the wire body possesses a tapering outside diameter at which the outside diameter of the wire body becomes smaller toward the distal-most end of the wire body. The projection projects radially outwardly from the wire body, and possesses a proximal portion terminating at a proximal-most end and a distal portion terminating at a distal-most end. The projection possesses a circumferentially continuous annular shape, with the proximal-most end of the projection being spaced distally from the proximal-most end of the wire body and the distal-most end of the projection being spaced proximally from the distal-most end of the wire body. The coating layer is formed of a resin material, and the projection is made of a material different from the resin material forming the coating layer. The coating layer possesses a proximal-most end and a distal-most end, with the proximal-most end of the coating later being located distally of the proximal-most end of the wire body, and the proximal-most end of the coating later possessing an outer diameter. The distal end of the projection contacts the proximal end of the coating layer, and the projection possesses a maximum outside diameter greater than the outside diameter of the proximal-most end of the coating layer to prevent a medical instrument from catching on the proximal-most end of the coating later if the proximal-most end of the coating later turns-up away from the wire body.

In accordance with another aspect, a guide wire includes a flexible elongate wire body possessing a distal-most end and a proximal-most end, a coating layer fixed to a distal portion of the wire body and formed of a resin material, and a projection fixed to the wire body at a position proximal of the coating layer. The coating layer possesses a proximal-most end at which the coating layer terminates at a position distally spaced from the proximal-most end of the wire body. The projection projects radially outwardly from the wire body and possesses a circumferentially continuous annular shape. The projection is made of a material different from the resin material forming the coating layer, and the projection possesses a distal end face and a proximal-most end, with the proximal-most end of the projection being spaced distally from the proximal-most end of the wire body. The distal end face of the projection faces the proximal-most end of the coating layer and directly contacts the proximal-most end of the coating layer. The projection possesses a maximum outside diameter greater than the outside diameter of the proximal-most end of the coating layer that is directly contacting the proximal-most end of the coating layer.

The proximal portion of the projection is preferably provided with an outside diameter tapering portion that gradually decreases in outside diameter toward a proximal end. The wire body can be a core wire, and the projection can be comprised of a member different from the core wire.

The projection is preferably comprised of a tubular or coiled member. The projection is preferably formed with a plurality of recesses in its outer circumferential surface. The recesses can each be a groove inclined relative to the longitudinal direction of the wire. At least part of the projection preferably covers a proximal portion of the coating layer. The projection is also preferably in engagement (contact) with the proximal portion of the coating layer.

It is preferable that the proximal portion of the coating layer includes a tapering portion that gradually decreases in outside diameter toward the proximal end. The resin material used to for the coating layer is preferably principally a urethane resin. The core wire preferably has a constant outside diameter section that is constant in outside diameter along a longitudinal direction of the wire, and the projection is disposed at the constant outside diameter section.

The guide wire makes it possible to rather securely inhibit or prevent a situation in which the proximal portion of the coating layer turns-up and a medical instrument such as a catheter with which the guide wire is used catches on the turned-up part.

DETAILED DESCRIPTION

Set forth below, initially with respect to FIG. 1 and FIGS. 2(a)-2(c), is a detailed description of an embodiment of a guide wire representing on example of the guide wire disclosed here. In the description which follows, for convenience of description, the right side in FIGS. 1 and 2(a)-2(c), (and also in FIGS. 3 to 7 described later) will be referred to as the "proximal end," and the left side will be referred to as the "distal end." To help facilitate an understanding of the disclosed guide wire, the guide wire is shown in a state of being shortened in a lengthwise direction and exaggerated in a thickness direction. It is thus to be understood that the ratio of a dimension in the lengthwise direction to a dimension in the thickness direction differs from the actual or practical ratio.

The guide wire 1 shown in FIG. 1 and FIGS. 2(a)-2(c) is a catheter guide wire for use in a state of being inserted in a lumen 201 of a catheter 20 (inclusive of an endoscope). The guide wire 1 includes an elongate wire body 2, a helical coil 4, and a distal-side coating layer 6 (hereafter referred to as "resin coating layer 6"). The overall length of the guide wire 1 is not particularly limited, though is preferably about 200 to 5,000 mm. The mean outside diameter of the guide wire 1 is also not specifically restricted, though is preferably about 0.2 to 1.2 mm.

In this embodiment, the wire body 2 has a flexible or pliable single core wire (wire) 3 extending continuously from the proximal-most end of the core wire 3 to the distal-most end of the core wire 3 and a proximal-side coating layer 7 (hereafter referred to as "coating layer 7") covering a part of the core wire ranging from an intermediate portion of the core wire to a proximal end of the core wire 3. Further, the wire body 2 has a projection member (projection) 5A disposed at a part, on the distal side relative to the coating layer 7, of the core wire 3. This "projection member 5A" will be described later. The wire body 2 may also have other components (e.g., another layer or the like). In addition, the coating layer 7 may be omitted.

In the illustrated embodiment, the core wire 3 is circular in cross-sectional shape, is solid (i.e., not hollow or tubular) and extends over substantially the whole length of the guide wire 1. The core wire 3 can be divided, according to the magnitude or size of the outside diameter, into a body section 32, a first taper section 33, a first constant outside diameter section 34, a second taper section 35, and a second constant outside diameter section 36, in this order from the proximal end to the distal end.

The body section 32 is a section which is substantially constant in outside diameter and which corresponds to a body section of the guide wire 1. In addition, the body section 32 is a section of the core wire 3 possessing the greatest outside diameter.

On the distal side of the body section 32 is disposed the first taper section 33. That is, the proximal-most end of the taper section 33 and the distal-most end of the body section 32 directly adjoin one another. The first taper section 33 gradually decreases in outside diameter in the distal direction. The outside diameter at a proximal-most end of the first taper section 33 is equal to the outside diameter of the body section 32.

On the distal side of the first taper section 33 is disposed the first constant outside diameter section 34. That is, the proximal-most end of the first constant outside diameter section 34 directly adjoins distal-most end of the first taper section 33. The first constant outside diameter section 34 is substantially constant in outside diameter, and its outside diameter is equal to the outside diameter of the first taper section 33 at the distal-most end of the first taper section 33.

On the distal side of the first constant outside diameter section 34 is disposed the second taper section 35. The proximal-most end of the second taper section 35 directly adjoins the distal-most end of the first constant outside diameter section 34. The second taper section 35 gradually decreases in outside diameter in the distal direction, in other words, it tapers. In addition, the outside diameter at the proximal-most end of the second taper section 35 is equal to the outside diameter of the first constant outside diameter section 34.

On the distal side of the second taper section 35 is disposed the second constant outside diameter section 36. The proximal-most end of the second constant outside diameter section 36 directly adjoins the second taper section 35. The second constant outside diameter section 36 is substantially constant in outside diameter, and its outside diameter is equal to the outside diameter at the distal-most end of the second taper section 35.

Thus, in the guide wire 1, the core wire 3 is provided with the first taper section 33 and the second taper section 35. This helps ensure that the flexibility of the core wire 3 gradually (continuously) increases along the distal direction from the vicinity of a boundary between the body section 32 and the first taper section 33. As a result, the flexibility of the guide wire 1 is increased. Accordingly, operability and safety in inserting the guide wire 1 into a living body are enhanced.

The taper angle of the first taper section 33 and that of the second taper section 35 may be the same or different. Further, each of the first taper section 33 and the second taper section 35 may be constant in taper angle along a longitudinal direction of the core wire 3, or may have a part where the taper angle varies along the longitudinal direction.

In addition, the length of a part ranging from the first taper section 33 to a distal end of the core wire 3 is not particularly limited; for example, this length is preferably 0.1 to 20%, more preferably 0.1 to 10%, based on the whole length of the guide wire 1.

Examples of the material for forming the core wire 3 include various metallic materials such as stainless steel, Ni—Ti alloys, Ni—Al alloys, Cu—Zn alloys and the like superelastic alloys, as well as resin materials having comparatively high rigidity. These materials may be used either singly or in combination of two or more of them.

In addition, a part which ranges from an intermediate portion of the first taper section 33 to the proximal end of the core wire 3 has an outer circumferential surface covered with the coating layer 7. The coating layer 7 can be formed for various purposes. One example of the various purposes is to reduce friction (sliding resistance) on the guide wire 1 so as to enhance slidablility, thereby enhancing operability of the guide wire 1.

To reduce the friction (sliding resistance) on the guide wire 1, the coating layer 7 is preferably formed from a material capable of reducing friction as will be described below. This helps ensure that the frictional resistance (sliding resistance) between the guide wire 1 and the inner circumferential surface 202 of the catheter 20 used with the guide wire 1 is reduced, whereby slidability is enhanced, and better operability of the guide wire 1 in the catheter 20 is realized. In addition, with the sliding resistance on the guide wire 1 lowered, kinking (bending) or torsion of the guide wire 1 can be more reliably prevented from occurring at the time when the guide wire 1 is moved and/or rotated within the catheter 20.

Examples of a material capable of reducing friction in the above-mentioned manner include polyolefin such as polyethylene and polypropylene, polyvinyl chloride, polyester (PET, PBT and the like), polyamide, polyimide, polyurethane, polystyrene, polycarbonate, silicone resin, fluoro-resin (PTFE, ETFE, PFA and the like), and composite materials of them. Particularly preferred among these materials is the fluoro-resin (or composite materials containing it). In this case, in addition to the above-mentioned enhancement of operability, there is obtained an advantage that coating of the core wire 3 can be relatively easily carried out in a condition where the resin material is heated by baking, spraying or the like method. In addition, particularly excellent adhesion is realized between the core wire 3 and the coating layer 7.

The thickness of the coating layer 7 is not particularly limited, and is appropriately set in consideration of the purpose, material, forming method and the like of the coating layer 7. Normally, the mean thickness is preferably about 1 to 100 μm, more preferably about 1 to 30 μm. Incidentally, the coating layer 7 may be a stack of two or more layers.

The outer circumferential surface of the core wire 3 may be subjected to treatment such as surface roughening, a chemical treatment or a heat treatment for enhancing the adhesion of the coating layer 7 and the resin coating layer 6. Further, an intermediate layer capable of enhancing the adhesion of the resin coating layer 6 and the coating layer 7 may be disposed.

The coil 4 is disposed, in an axially extending manner, along the outer circumference of a distal portion of the core wire 3 (wire body 2), specifically, along the outer circumference of the second constant outside diameter section 36 and the outer circumference of a part of the core wire 3 extending to an intermediate portion of the second taper section 35 of the core wire 3 in the configuration shown in the drawings. The coil 4 is a member which is obtained by helically winding an elementary wire and which covers or surrounds the outer circumference of the distal portion of the core wire 3. The core wire 3 passes through a substantially central part of the inside of the coil 4. In addition, in the configuration shown in the drawings, the coil 4 is not in contact with the core wire 3; in other words, the inner surface of the coil 4 is spaced from the outer circumference of the core wire 3. This configuration is not restrictive however. For example, the coil 4 may be in contact with the outer circumference of the core wire 3.

In the configuration shown in the drawings, in a condition where no external force is applied or exerted, the coil 4 has gaps between axially adjacent loop portions of the elementary wire wound in a helical shape. However, a configuration may also be adopted in which, in the condition where no external force is applied, the axially adjacent loop portions of the elementary wire wound in the helical shape are closely arranged without any gap therebetween.

In addition, in the case of this embodiment, the coil 4 is formed by use of an elementary wire which is circular in cross section. However, this configuration is not restrictive. For example, the elementary wire may be elliptic, tetragonal (particularly, rectangular) or the like in cross section.

The coil 4 is preferably formed from a metallic material, examples of which include stainless steel, superelastic alloys, cobalt alloys, noble metals such as gold, platinum and tungsten, and alloys containing them (e.g., platinum-iridium alloy). Especially, in a case where the coil 4 is formed from a radiopaque material (material which has radiopacity) such as noble metals, radiopacity can be imparted to the guide wire 1, and the guide wire 1 can be inserted into a living body while confirming the position of its distal portion under radioscopy, which is preferable. The coil 4 may be formed of one material on the distal side (distal end portion) and formed of another material on the proximal side (proximal end portion). For example, the coil 4 may be composed of a coil of a radiopaque material on the distal side and composed of a coil of a comparatively radiolucent material (stainless steel or the like) on the proximal side.

A proximal portion of the coil 4 is fixed to the second taper section 35 of the core wire 3 through a fixing material 81, and a distal portion of the coil 4 is fixed to the second constant outside diameter section 36 of the core wire 3 through a fixing material 82. The fixing materials 81 and 82 are each composed of solder (brazing material), for example.

In addition, the guide wire 1 has the resin coating layer 6 which collectively covers a distal portion of the core wire 3, the coil 4, and the fixing materials 81 and 82. The resin coating layer 6 is in contact with the outer circumference of the distal portion of the core wire 3. In the illustrated embodiment, the resin coating layer 6 enters the coil 4 (e.g., the resin is located between the axially adjacent windings), an alternative configuration can be adopted in which the resin coating layer 6 does not enter the coil 4.

The resin coating layer 6 can be formed for various purposes. Examples of the purposes include enhancement of safety in inserting the guide wire 1 into a blood vessel or the like, in addition to enhancement of operability of the guide wire 1 through raising slidability like in the case of the coating layer 7. Such a resin coating layer 6 is formed from a material rich in flexibility (flexible material or elastic material), which is not particularly restricted. Examples of the material include the same materials as those for the coating layer 7, various rubber materials such as latex rubber and silicone rubbers, and composite materials obtained by combining two or more of them. Particularly preferred among these materials are urethane resins. Where the resin coating layer 6 is formed mainly of a urethane resin, flexibility of the distal portion of the guide wire 1 is more enhanced. Therefore, at the time of insertion into a blood vessel or the like, it is possible to more securely prevent an inner wall of the blood vessel or the like from being damaged; thus, extremely high safety is ensured.

A distal end surface 61 of the resin coating layer 6 is rounded. This makes it possible to help prevent the distal end surface 61 from damaging an inner wall of a lumen such as a blood vessel.

Figure 2:
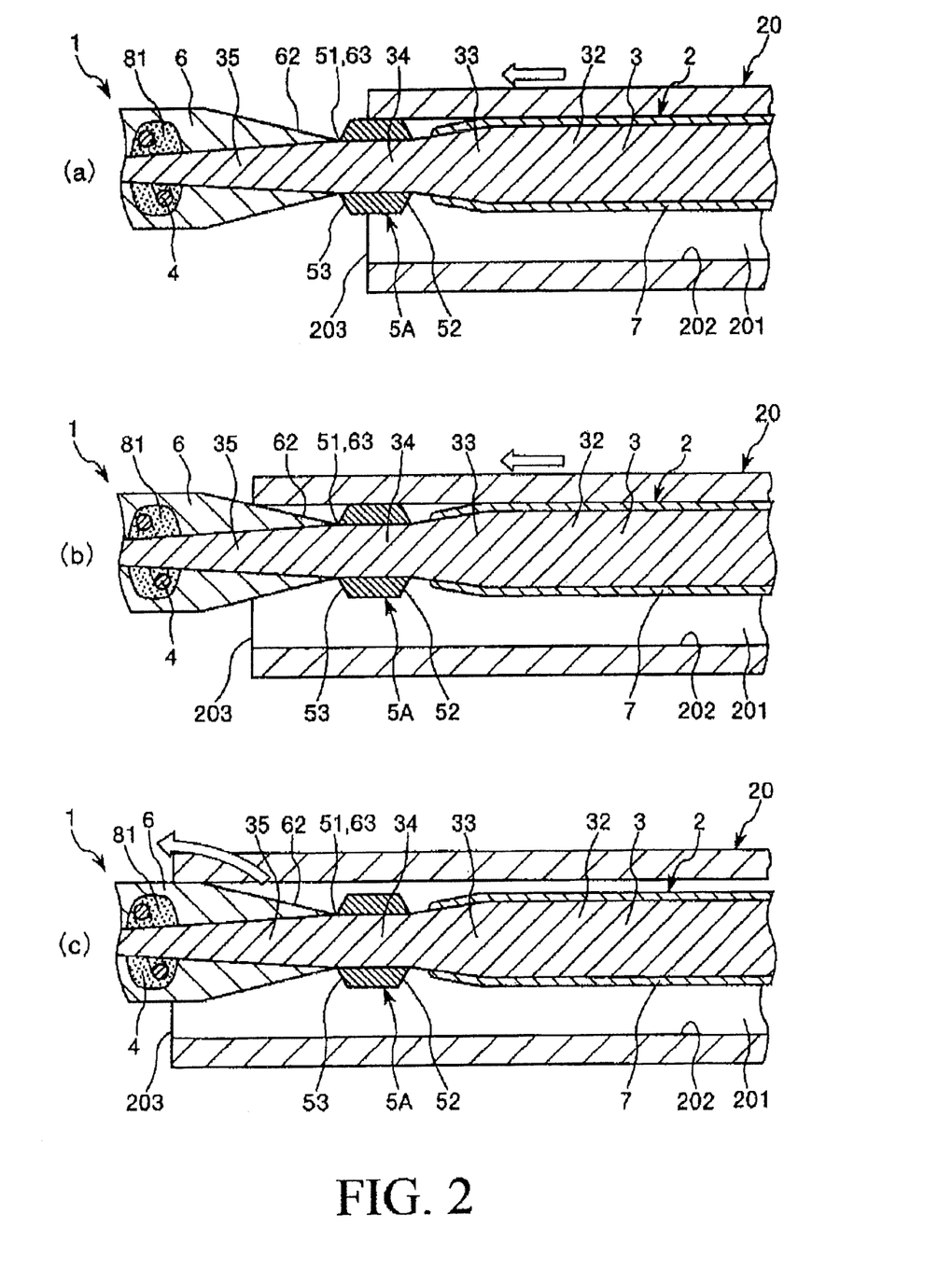
FIGS. 2(a)-2(c) are longitudinal cross-sectional views illustrating states in use of the guide wire shown in FIG. 1.

At a proximal portion of the resin coating layer 6 is formed a tapering portion 62 that gradually decreases in outside diameter toward a proximal direction. This helps ensure that, when the catheter 20 is pushed in toward the distal direction, as shown in FIG. 2, a distal end 203 of the catheter 20 can relatively easily ride over the proximal portion of the resin coating layer 6, that is, the tapering portion 62. Therefore, the pushing-in operation can be carried out easily and assuredly. In addition, the tapering portion 62 formed at a position where the core wire 3 gradually diminishes helps ensure that rigidity gradually decreases from the proximal side toward the distal end. This configuration is advantageous in that operability of the guide wire 1 is enhanced.

The taper angle of the tapering portion 62 is constant along the longitudinal direction of the core wire 3 in this embodiment. The taper angle is not particularly limited; for example, it is preferably 1 to 90 degrees, more preferably to 20 degrees. The tapering portion 62 may have a part where the taper angle varies along the longitudinal direction.

In addition, a proximal end 63 of the resin coating layer 6 is located at a boundary between the first constant outside diameter section 34 and the second taper section 35 of the core wire.

The resin coating layer 6 may have particles (filler) dispersed therein and formed of a radiopaque material. In this case, radiopacity can be imparted to the guide wire 1, so that the guide wire 1 can be inserted into a living body while confirming the position of its distal portion under radioscopy. The radiopaque material is not specifically restricted. Examples include noble metals such as platinum and tungsten, and alloy materials containing them.

The thickness of the resin coating layer 6 is not particularly limited, and is appropriately set in consideration of the purpose, material, forming method and the like of the resin coating layer 6. Normally, the mean thickness is preferably about 100 to 500 μm, more preferably about 150 to 300 μm. The resin coating layer 6 may be a stack of two or more layers.

As above-mentioned, the guide wire 1 has the projection member 5A projecting at an outer circumferential portion of the core wire 3. The projection member 5A is composed of a tubular (ring-shaped) member which is disposed and fixed on the first constant outside diameter section 34 of the core wire and ranges over the entire circumference of the outer circumferential portion. That is, the projection member 5A possesses a circumferentially continuous annular shape so that the projection member 5A extends circumferentially over the entire outer circumference of the first constant outside diameter section 34. In addition, the distal end 51 of the projection member 5A is in contact with the proximal end 63 of the resin coating layer 6. Furthermore, the maximum outside diameter $\phi d1$ of the projection member 5A is greater than the outside diameter of the part of the guide wire immediately adjoining the distal end 51 of the projection member 5A, namely the outside diameter $\phi d2$ of the proximal end 63 of the resin coating 6. Such a projection member 5A helps ensure that the proximal end 63 is located on the inner side relative to the maximum outside diameter $\phi d1$ of the projection member 5A. The proximal end 63 with the comparatively small layer thickness represents a part of the resin coating layer 6 that is most easily peelable (namely, turnable up) from the core wire 3, depending on the use conditions for the guide wire 1.

As shown in FIG. 2(a), illustrating an attempt to push the catheter 20 forward to a target site in a body lumen by use of the guide wire 1 having the projection member 5A, the distal end 203 of the catheter 20 slides sequentially on the coating layer 7 and the projection member 5A of the guide wire 1. Then, eventually, the distal end 203 comes to abut on the tapering portion 62 of the resin coating layer 6, as shown in FIG. 2(b). When the catheter 20 is further pushed forward starting from the condition shown in FIG. 2(b), the distal end 203 can climb up the tapering portion 62 of the resin coating layer 6 (see FIG. 2(c)). Therefore, the distal end 203 can be made to arrive at the target site in the body lumen.

During a period after riding over the projection member 5A until abutting on the tapering portion 62, the distal end 203 of the catheter 20 is prevented from making contact with the proximal end 63 of the resin coating layer 6 which is located on the inner side relative to the maximum outside diameter $\phi d1$ of the projection member 5A. As a result, even if the proximal end 63 has been somewhat turned up, the distal end 203 of the catheter 20 is relatively securely prevented from being caught on the proximal end 63.

In addition, the projection member 5A is formed, at its proximal portion, with a proximal-side tapering portion (outside diameter tapering portion) 52 where the outside diameter gradually decreases toward the proximal direction. Similarly, the projection member 5A is formed, at its distal portion, with a distal-side tapering portion (outside diameter tapering portion) 53 where the outside diameter gradually decreases toward the distal direction. The distal-side tapering portion 53 may be omitted. In the guide wire 1, since the proximal-side tapering portion 52 is formed, the distal end 203 of the catheter 20 being moved from the proximal side can smoothly ride over the projection member 5A (see FIG. 2(a)).

The maximum outside diameter $\phi d1$ of the projection member 5A is smaller than (or equal to) the maximum outside diameter $\phi d4$ of the resin coating layer 6. That is, the maximum outside diameter $\phi d1$ of the projection member 5A is not greater than the maximum outside diameter $\phi d4$ of the resin coating layer 6. Also, the length L1 of the projection member 5A is smaller than the length L2 of the resin coating layer 6. These relative relationships help ensure that, for example when the guide wire 1 is moved within a body lumen, at the distal portion, the resin coating layer 6 having relatively high slidability abuts on a wall part constituting the body lumen, with priority over the projection member 5A. This helps enable the guide wire 1 to be operated without reduction in operability.

As described above, the projection member 5A is disposed on the first constant outside diameter section 34. In contrast, if for example the projection member 5A is disposed on the first taper section 33, the projection member 5A is liable to be coming out of position on the first taper section 33 by being pushed by the catheter 20 being pushed in the distal direction. Because the projection member 5A is disposed on the first constant outside diameter section 34, such displacement described above is inhibited or prevented from occurring even when pushed by the catheter 20 being pushed in from the proximal direction.

Figure 1:
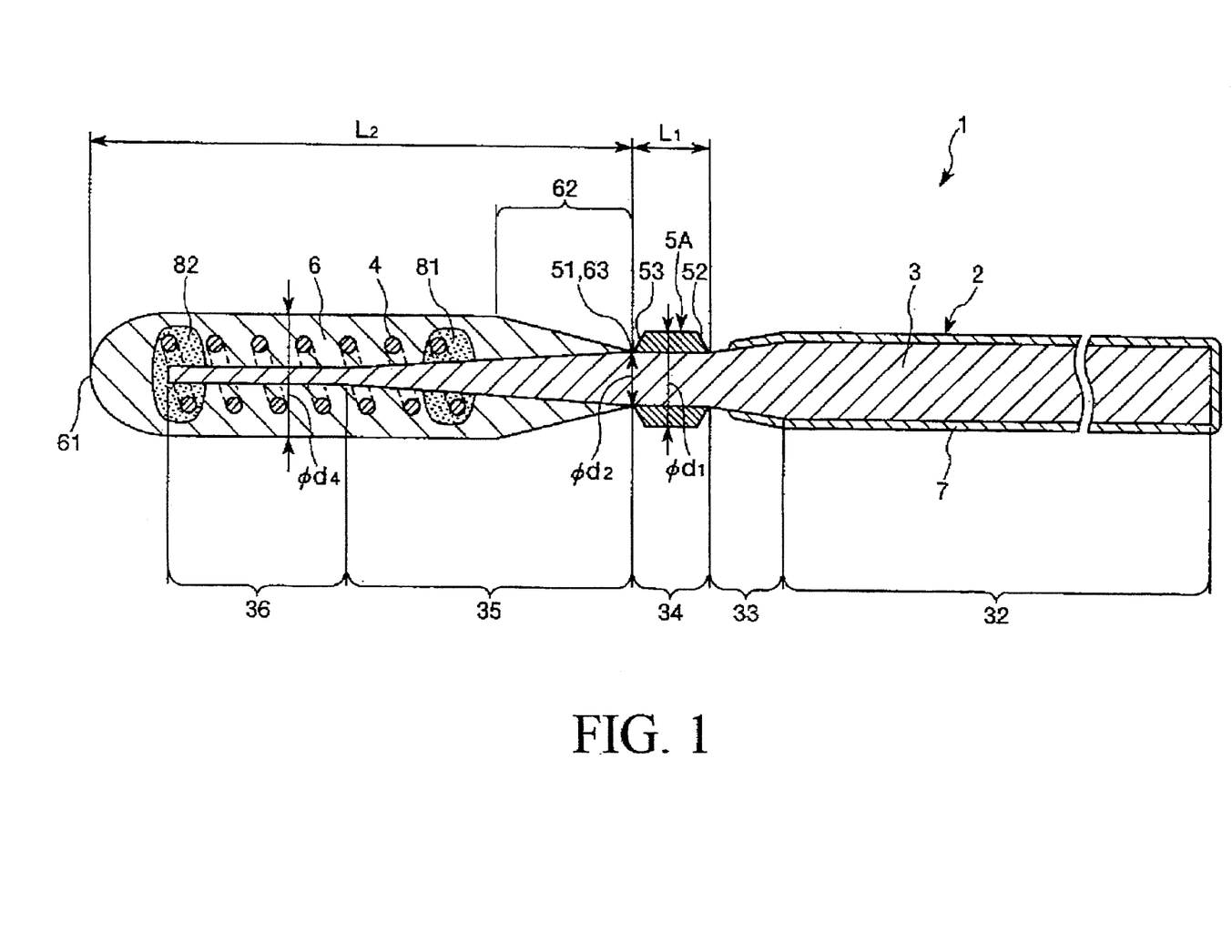
FIG. 1 is a longitudinal cross-sectional view of a first embodiment of a guide wire constituting one example of the guide wire disclosed here.

While the projection member 5A is disposed over the whole length (entire axial extent) of the first constant outside diameter section 34 in the configuration shown in FIG. 1, the guide wire disclosed here is not limited in that way. For example, the projection member 5A may be disposed on a part of the first constant outside diameter section 34 in the longitudinal direction. In other words, while the length of the projection member 5A is equal to the entire length of the first constant outside diameter section 34 in the illustrated embodiment, this is not restrictive. For example, the projection member 5A may be axially shorter than the first constant outside diameter section 34.

A method for fixing the projection member 5A to the first constant outside diameter section 34 is not limited to a specific method. Examples include fitting, caulking, adhesion (adhesion by use of an adhesive or a brazing material), fusing (heat fusing, high-frequency fusing, ultrasonic fusing, etc.), and welding. In addition, where a method by adhesion is adopted as the method for fixing the projection member 5A, the adhesive or brazing material protruding to the proximal side of the projection member 5A is preferably subjected to rounding or chamfering.

The projection member 5A is formed from a material which is harder than the resin material constituting the resin coating layer 6. The projection 5A is thus made of a material different from the material (resin material) forming the coating layer 3. Examples of such harder material include a metallic material or a hard resin material. The metallic material is not particularly limited, and examples include stainless steel, titanium, titanium alloys, Ni—Ti alloys, aluminum, gold, and platinum. Examples of the hard resin material include polycarbonate, polyamide (nylon), polyethylene terephthalate, polyacetal, and polyphenylene sulfide. The material or material composition forming the projection 5A is preferably also different from (not the same as) the material or material composition forming the coating layer 7.

When such a material is used, the pushing force exerted from the catheter 20 being moved toward the distal side can be received rather assuredly. Therefore, the proximal end 63 of the resin coating layer 6 can be protected from the distal end 203 of the catheter 20. Consequently, the distal end 203 of the catheter 20 can be more securely prevented from catching on the proximal end 63 of the resin coating layer 6.

Figure 3:
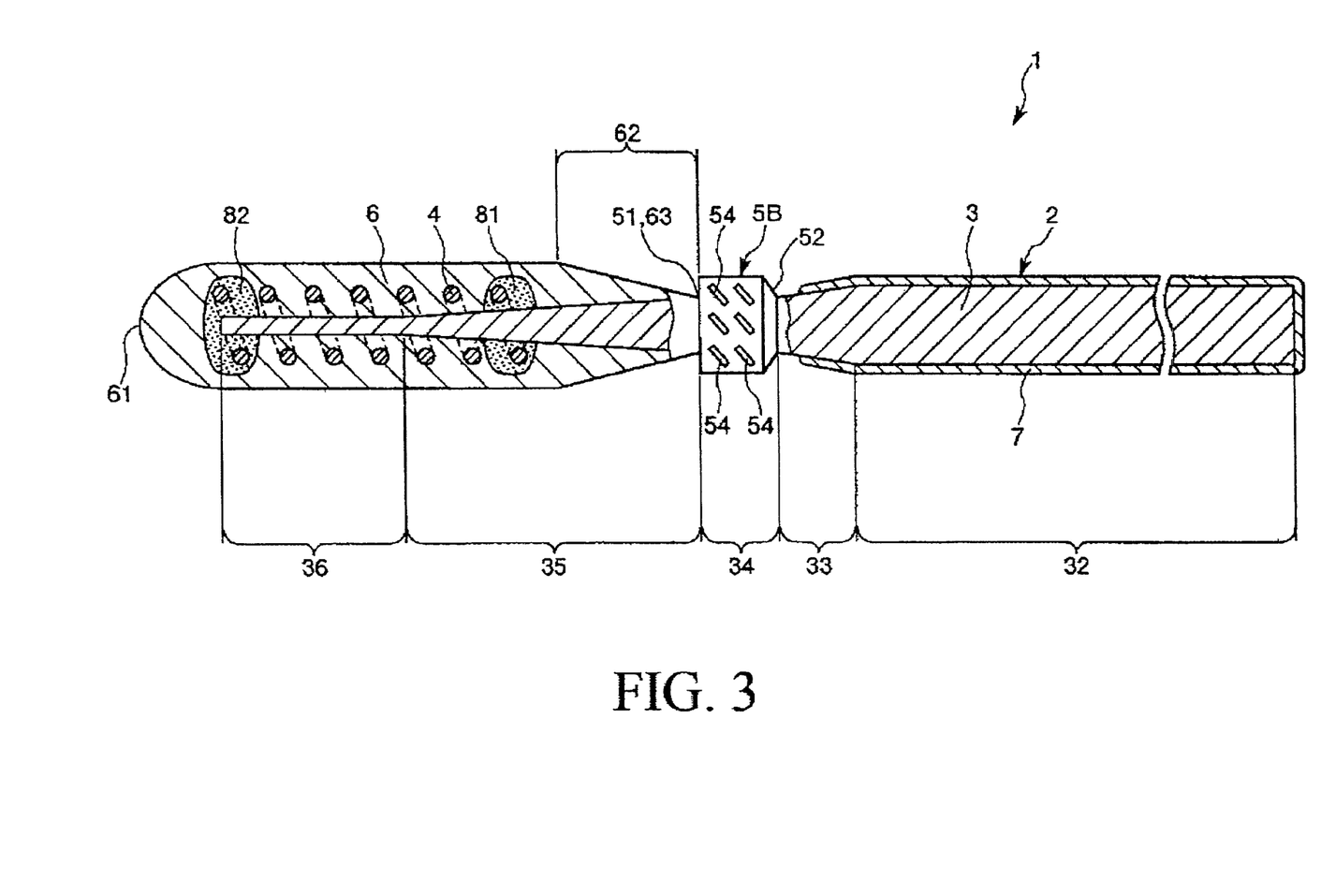
FIG. 3 is a partly longitudinal cross-sectional view of a second embodiment of the guide wire.

FIG. 3 illustrates a second embodiment of the guide wire disclosed here. The description below will primarily focus on differences between this second embodiment and the above-described embodiment. Features associated with this second embodiment of the guide wire that are the same as those associated with the embodiment described above are identified by common reference numerals, and a detailed description of such features is not repeated.

This second embodiment is the same as the above-described first embodiment except for a difference in the configuration of the projection member.

In the guide wire 1 shown in FIG. 3, a projection member 5B is formed with a plurality of grooves (recesses) 54 in its outer circumferential portion. The grooves 54 are each inclined relative to the longitudinal direction of the wire. Each of the grooves 54 is preferably a slit piercing a wall part of the projection member 5B.

These grooves 54 help the projection member 5B itself to be curved relatively easily. Therefore, trackability of the guide wire 1, particularly at the projection member 5B, for a curved body lumen is enhanced.

The recesses formed in the outer circumferential surface of the projection member 5B are not restricted to the illustrated grooves 54. For example, the recesses may be those which are, for example, circular or square in side view.

In addition, in the projection member 5B, a distal-side tapering portion 53 is omitted. However, the distal-side tapering portion 53 may be provided like the projection member 5A shown in FIG. 1.

Figure 4:
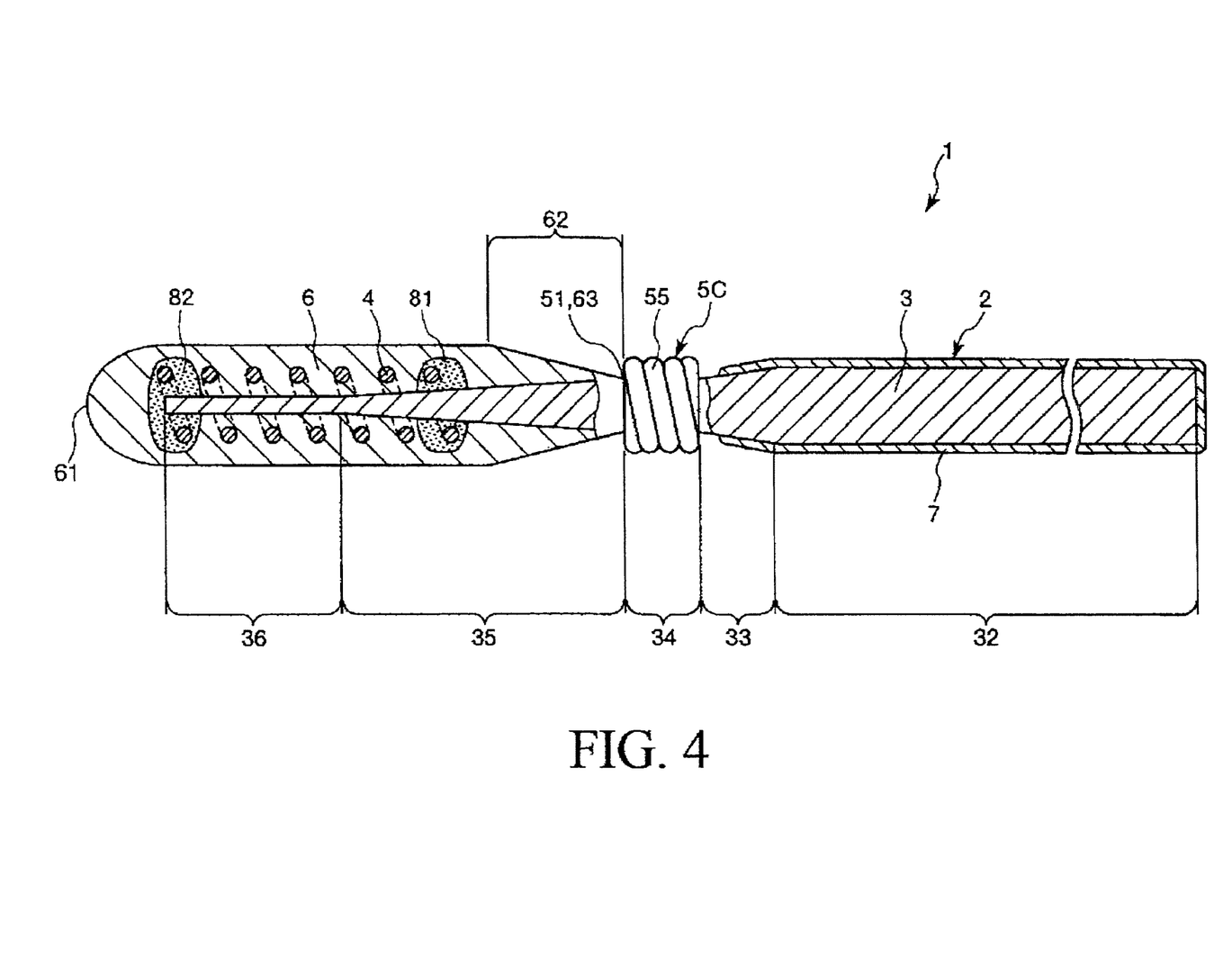
FIG. 4 is a partly longitudinal cross-sectional view of a third embodiment of the guide wire.

FIG. 4 is a partly longitudinally sectional side view showing a third embodiment of the guide wire disclosed here. The description below will primarily focus on differences between this third embodiment and the above-described embodiments. Features associated with this third embodiment of the guide wire that are the same as those associated with the embodiment described above are identified by common reference numerals, and a detailed description of such features is not repeated.

This embodiment is the same as the above-described first embodiment except for a difference in the configuration of the projection member.

The guide wire 1 shown in FIG. 4 includes a projection member 5C composed of a coil formed by helically winding an elementary wire 55 around the axis of the core wire 3. This helps ensure that the projection member 5C itself can be curved rather easily. Therefore, trackability of the guide wire 1, particularly at the projection member 5C, for a curved body lumen is enhanced.

The guide wire shown in FIG. 4 is configured so that the projection member 5C has adjacent loop portions of the elementary wire 55 in close contact with each other. However, the guide wire is not limited to this configuration. For example, the adjacent loop portions of the elementary wire 55 may be spaced from each other.

Figure 5:
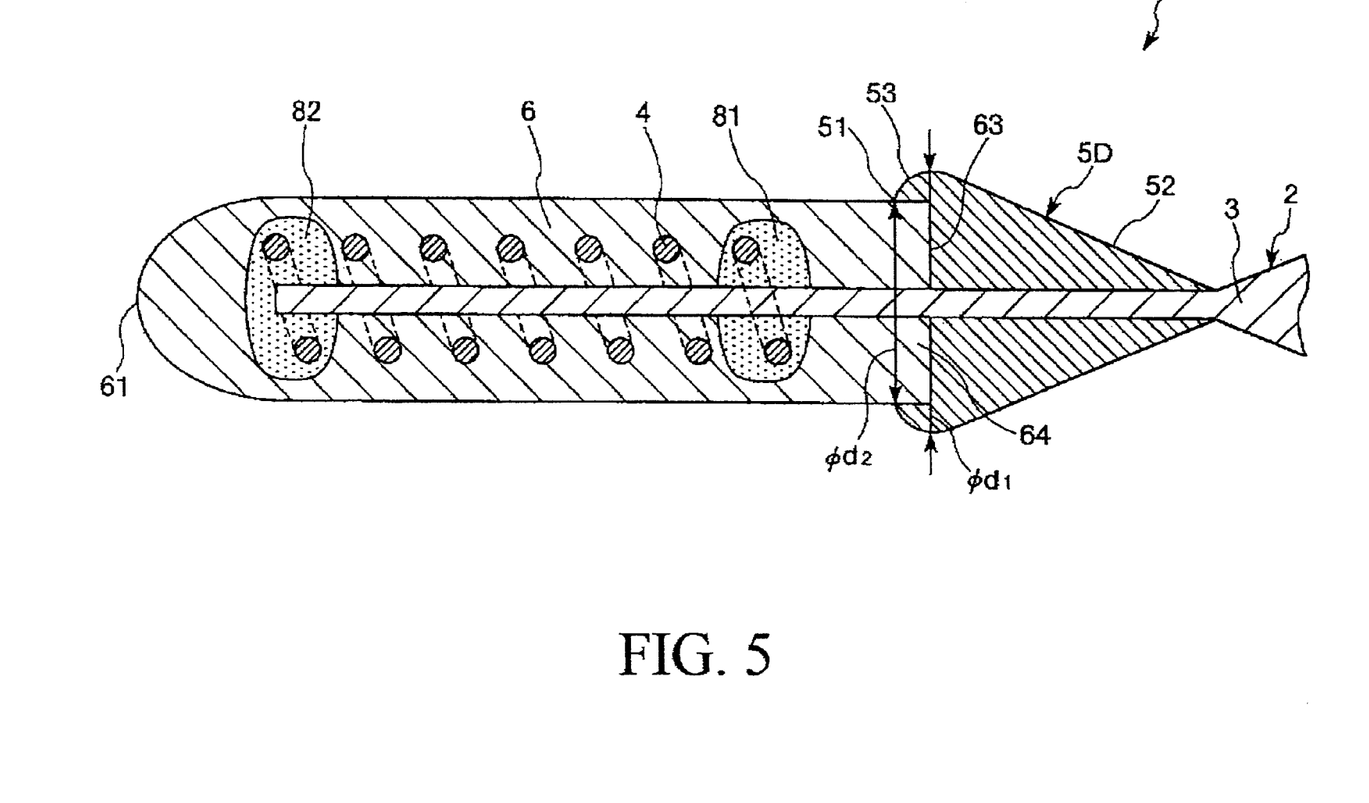
FIG. 5 is a longitudinal cross-sectional view of a portion of the guide wire according to a fourth embodiment.

FIG. 5 is a longitudinal sectional view showing a fourth embodiment of the guide wire according to the present invention. The description below will primarily focus on differences between this fourth embodiment and the above-described embodiments. Features associated with this fourth embodiment of the guide wire that are the same as those associated with the embodiment described above are identified by common reference numerals, and a detailed description of such features is not repeated.

This embodiment is the same as the above-described first embodiment except for a difference in the condition in which the projection member is disposed.

A projection member 5D in the guide wire 1 shown in FIG. 5 has the distal-side tapering portion 53 disposed so that it is laid on (axially overlaps) a proximal portion 64 of the resin coating layer 6. This embodiment of the guide wire 1 is configured so that the maximum outside diameter $\phi d1$ of the projection member 5D is greater than the outside diameter $\phi d2$ of the part at which the distal end 51 of the projection member 5D of the resin coating layer 6 is located, like in the guide wire 1 of the above-described first embodiment. This helps ensure that, when the catheter 20 is pushed forward in the distal direction along the guide wire 1, the distal end 203 of the catheter 20 is more securely prevented from being caught on the proximal end 63 of the resin coating layer 6.

In the resin coating layer 6 of this embodiment, unlike in the resin coating layer 6 of the above-described first embodiment, the tapering portion 62 is omitted from the proximal portion 64. That is, the proximal end portion of the resin coating layer 6 possesses a constant outer diameter. However, the guide wire is not limited to this configuration. For example, the tapering portion 62 may be formed, like in the resin coating layer 6 of the above-described first embodiment or a fifth embodiment which will be described below.

In addition, in the projection member 5D, the length of the proximal-side tapering portion 52 is greater than the length of the distal-side tapering portion 53.

Figure 6:
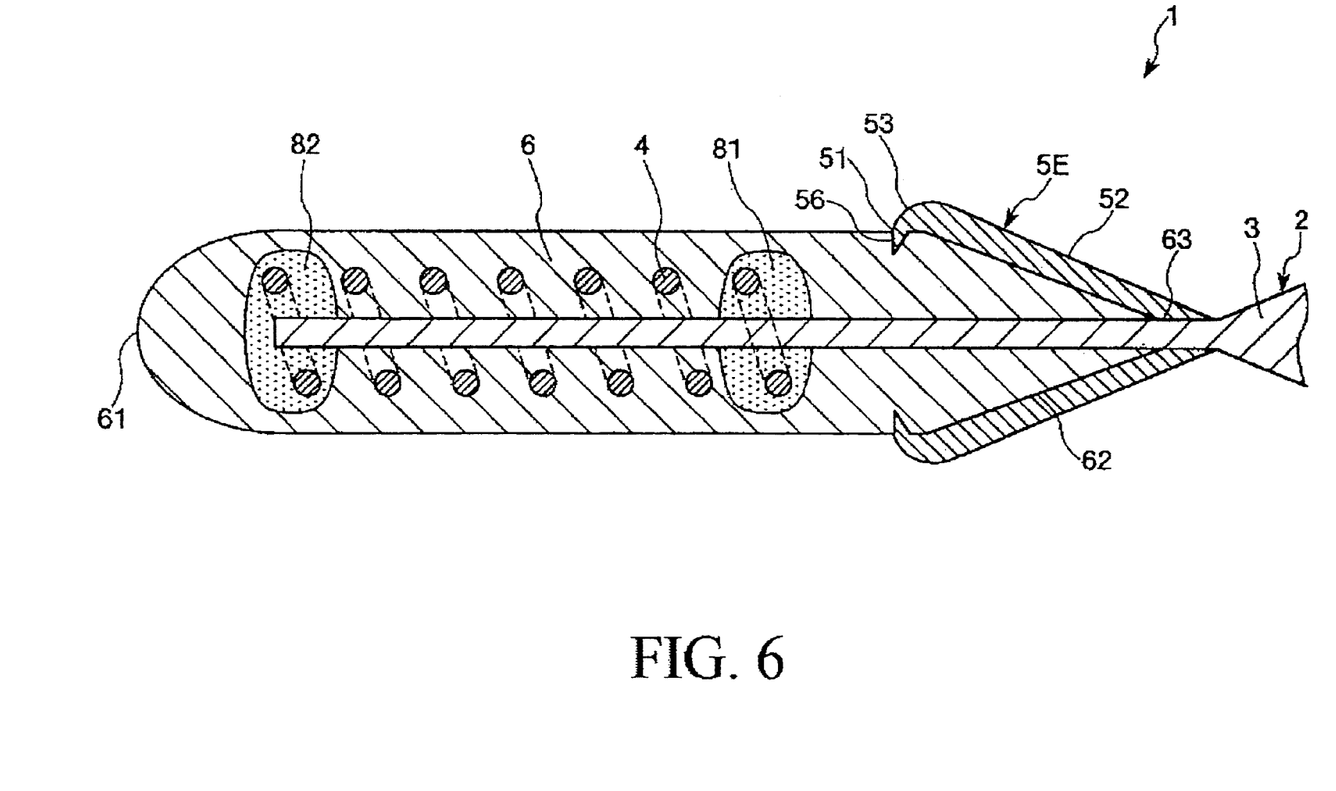
FIG. 6 is a longitudinal cross-sectional view of a portion of the guide wire according to a fifth embodiment.

FIG. 6 is a longitudinal sectional view showing the fifth embodiment of the guide wire. The description below will primarily focus on differences between this fifth embodiment and the above-described embodiments. Features associated with this fifth embodiment of the guide wire that are the same as those associated with the embodiment described above are identified by common reference numerals, and a detailed description of such features is not repeated.

This embodiment is the same as the above-described fourth embodiment except for a difference in the configuration of the projection member.

In the guide wire 1 shown in FIG. 6, a projection member 5E has an engaging section 56 which engages the resin coating layer 6. This engaging section 56 is composed of at least one claw projecting at a distal inner circumferential portion of the projection member 5E. The engaging section 56 contacts the radially outwardly facing outer circumferential surface of the resin coating layer 6.

Such a projection member 5E is securely prevented from being unwillingly peeled from the resin coating layer 6 during use of the guide wire 1. Especially, this produces an effect when the proximal end of the resin coating layer 6 passes through a curved part, and can help prevent a gap from being generated between the resin coating layer 6 and the projection member 5E.

Figure 7:
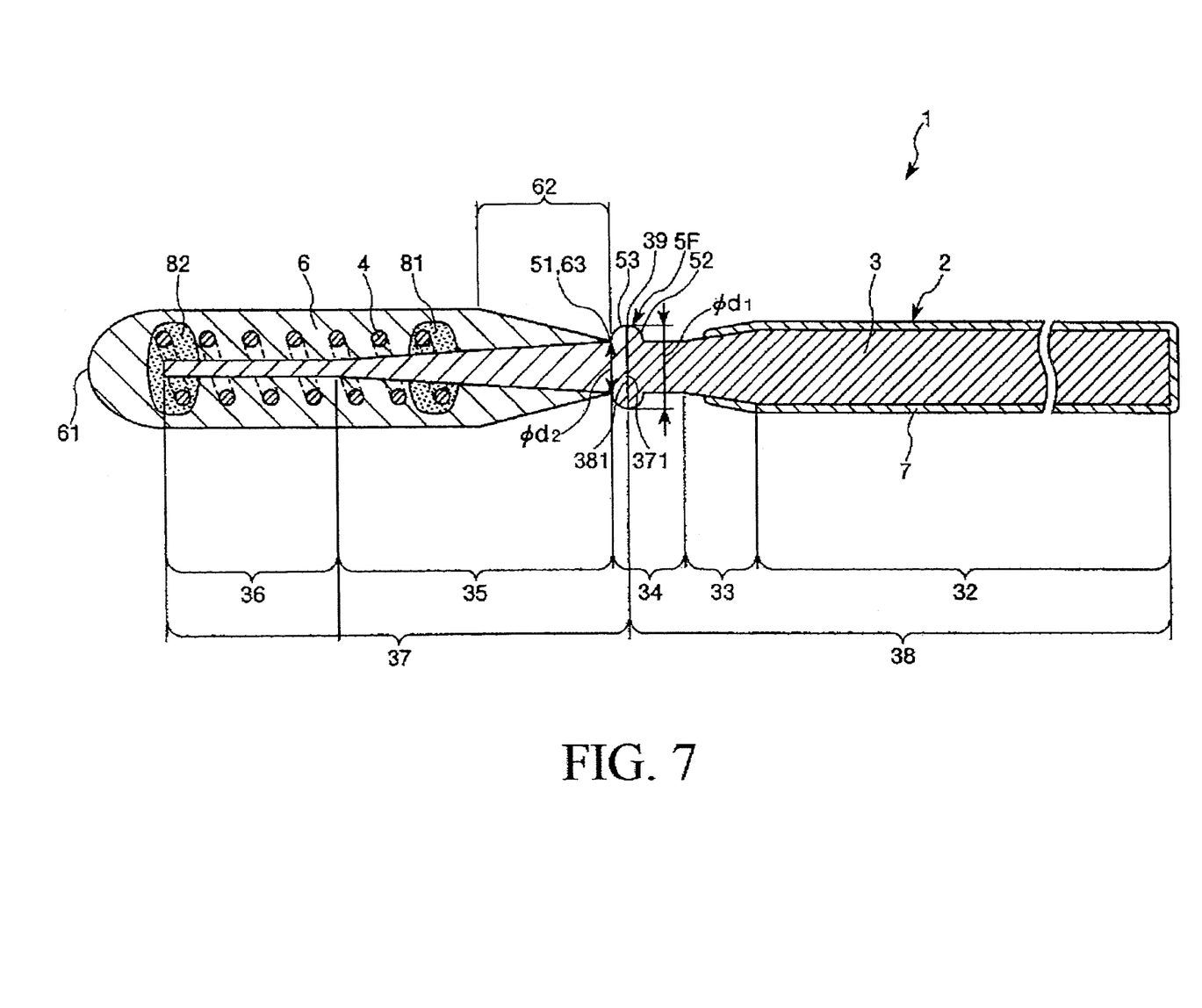
FIG. 7 is a longitudinal cross-sectional view of a sixth embodiment of the guide wire.

FIG. 7 is a longitudinal sectional view showing a sixth embodiment of the guide wire according to the present invention. The description below will primarily focus on differences between this sixth embodiment and the above-described embodiments. Features associated with this sixth embodiment of the guide wire that are the same as those associated with the embodiment described above are identified by common reference numerals, and a detailed description of such features is not repeated.

This embodiment is the same as the above-described first embodiment except for a difference in the state in which the projection is formed.

In the guide wire 1 shown in FIG. 7, the core wire 3 is composed of a first wire 37 and a second wire 38. A proximal end surface 371 of the first wire 37 and a distal end surface 381 of the second wire 38 are put into pressure contact with each other while the first wire 37 and the second wire 38 are being applied with a predetermined voltage by a butt welding machine. The pressure contact causes a molten layer to be formed at a joint 39, whereby the first wire 37 and the second wire 38 are firmly connected to each other. In the configuration shown, the joint 39 is located at an intermediate position of the first constant outside diameter section 34 in the longitudinal (axial) direction of the wire.

Since a proximal portion of the first wire 37 and a distal portion of the second wire 38 are each deformed and raised by the above-mentioned pressure contact, a projection 5F is formed in the vicinity of the joint 39. The projection 5F has its distal end 51 in contact with the proximal end 63 of the resin coating layer 6. In addition, the maximum outside diameter $\phi d1$ of the projection 5F is greater than the outside diameter $\phi d2$ of the proximal end 63 of the resin coating layer 6.

Like the projection member 5A in the above-described first embodiment, such a projection 5F helps ensure that, when the catheter 20 is pushed forward in the distal direction along the guide wire 1, the distal end 203 of the catheter 20 is more securely prevented from being caught on the proximal end 63 of the resin coating layer 6.

The first wire 37 and the second wire 38 may be formed from the same material or from different materials. Where the same material is adopted, each of the first wire 37 and the second wire 38 may be formed from, for example, a Ni—Ti alloy or stainless steel. Where different materials are used, the first wire 37 may be formed from, for example, a Ni—Ti alloy, and the second wire 38 may be formed from, for example, stainless steel.

While the guide wire disclosed here has been described above as examples in reference to the embodiments shown in the drawings, the guide wire disclosed here is not limited to these embodiments. Each of the components of the guide wire can be replaced by another component of arbitrary configuration that can exhibit an equivalent function. And additional components may be added.

In addition, the guide wire disclosed here can be configured by a combination of two or more configurations (characteristics) of the above-described embodiments.

While the proximal-side coating layer is spaced from the proximal end of the projection in each of the embodiments, the guide wire is not limited in this regard. For example, the proximal-side coating layer may be in contact with the proximal end of the projection. In this case, just like the way that the projection prevents a proximal-side portion of the distal-side coating layer from turning up, the projection can also prevent a distal-side portion of the proximal-side coating layer from turning up.

The guide wire disclosed in the several examples here is a guide wire having a flexible elongate wire body and a coating layer which covers a distal portion of the wire body and is formed from a resin material. The wire body has a projection projecting along the entire circumference of an outer circumferential portion thereof. The projection has its distal portion in contact with a proximal portion of the coating layer. The maximum outside diameter of the projection is greater than the outside diameter of the coating layer being in contact with the projection. Therefore, when a medical instrument such as a catheter (representatively made to be "catheter") for use in combination with the guide wire is pushed forward along the guide wire toward a target site in a living lumen, a distal end of the catheter slides on the projection of the guide wire. When the catheter is further pushed forward, the distal end of the catheter comes into contact with a portion, on the distal side relative to the proximal portion, of the coating layer. As a result, the distal end of the catheter is prevented from making contact with a proximal-side part of the coating layer during a period after riding over the projection until coming into contact with the portion, on the distal side relative to the proximal portion, of the coating layer. This part might peel, depending on the conditions in which the guide wire is used. Since the distal end of the catheter is prevented from making contact with the proximal-side part of the coating layer, it is ensured that, even if the proximal-side part of the coating layer is peeled, the distal end of the catheter is securely prevented from being caught on the peeled part.

The detailed description above describes a guide wire according to several embodiments disclosed by way of example. The invention here is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire comprising:
    a flexible elongate solid wire body possessing a distal portion terminating at a distal-most end and a proximal portion terminating at a proximal-most end, at least a part of the distal portion of the wire body possessing a tapering outside diameter at which the outside diameter of the wire body becomes smaller toward the distal-most end of the wire body;
    a projection fixed to the wire body, the projection projecting radially outwardly from the wire body, the projection possessing a proximal portion terminating at a proximal-most end and a distal portion terminating at a distal-most end, the projection possessing a circumferentially continuous annular shape, the proximal-most end of the projection being spaced distally from the proximal-most end of the wire body and the distal-most end of the projection being spaced proximally from the distal-most end of the wire body;

a coating layer fixed to and covering at least a part of the distal portion of the wire body, the coating layer being formed of a resin material, the projection being made of a material different from the resin material forming the coating layer, the coating layer possessing a proximal-most end and a distal-most end, the proximal-most end of the coating layer being located distally of the proximal-most end of the wire body, the proximal-most end of the coating layer possessing an outer diameter;

the coating layer possessing a proximal-most end point, the projection possessing a distal-most end point, and the distal-most end point of the projection contacting the proximal-most end point of the coating layer; and the projection possessing a maximum outside diameter greater than the outside diameter of the proximal-most end point of the coating layer to prevent a medical instrument from catching on the proximal-most end point of the coating layer if the proximal-most end point of the coating layer turns-up away from the wire body.

2. The guide wire according to claim 1, wherein the coating layer is continuous from the distal-most end of the coating layer to the proximal-most end of the coating layer and covers the distal-most end of the wire body.

3. The guide wire according to claim 1, wherein the coating layer is a first coating layer, and further comprising a second coating layer covering the proximal portion of the wire body and possessing a distal-most end positioned proximally of the proximal-most end of the projection.

4. The guide wire according to claim 1, wherein the proximal-most end of the coating layer directly contacts the distal-most end of the projection.

5. A guide wire comprising:
a flexible elongate wire body possessing a distal-most end and a proximal-most end;
a coating layer fixed to a distal portion of the wire body and formed of a resin material, the coating layer possessing a proximal-most end point at which the coating layer terminates at a position distally spaced from the proximal-most end of the wire body, the coating layer possessing an outer diameter at the proximal-most end point of the coating layer;
a projection fixed to the wire body at a position proximal of the coating layer, the projection projecting radially outwardly from the wire body and possessing a circumferentially continuous annular shape, the projection being made of a material different from the resin material forming the coating layer, the projection possessing a distal-most end point and a proximal-most end, the proximal-most end of the projection being spaced distally from the proximal-most end of the wire body;
the distal-most end point of the projection facing the proximal-most end point of the coating layer and directly contacting the proximal-most end point of the coating layer; and
the projection possessing a maximum outside diameter greater than the outside diameter of the proximal-most end point of the coating layer that is directly contacting the distal-most end point of the projection.

6. The guide wire according to claim 5, wherein the coating layer is continuous from the distal-most end of the coating layer to the proximal-most end of the coating layer and covers the distal-most end of the wire body.

7. The guide wire according to claim 5, wherein the coating layer is a first coating layer, and further comprising a second coating layer covering the proximal portion of the wire body and possessing a distal-most end positioned proximally of the proximal-most end of the projection.

8. The guide wire according to claim 5, wherein the projection possesses a proximal portion possessing a tapering outside diameter at which the outside diameter of the proximal portion becomes gradually smaller towards the proximal-most end of the projection.

9. The guide wire according to claim 5, wherein the wire body is made of a material different from the material forming the projection.

10. The guide wire according to claim 5, wherein the projection is a tubular member or a coiled member.

11. The guide wire according to claim 5, wherein the proximal-most end of the coating layer directly contacts the distal-most end of the projection.

12. A guide wire comprising:
a flexible elongate wire body;
a coating layer covering a distal portion of the wire body and formed of a resin material, the coating layer possessing an outer diameter and a proximal-most end point;
the wire body including a projection which projects along an entire circumference of an outer circumferential portion of the wire body;
the projection possessing a distal-most end point in contact with the proximal-most end point of the coating layer; and
the projection possessing a maximum outside diameter greater than the outside diameter of the proximal-most end point of the coating layer that is in contact with the distal-most end point of the projection.

13. The guide wire according to claim 12, wherein the projection possesses a proximal portion having an outside diameter tapering portion that gradually decreases in outside diameter toward the proximal-most end of the projection.

14. The guide wire according to claim 12, wherein the wire body is a core wire, and the projection is comprised of a member different from the core wire and fixed to the core wire member.

15. The guide wire according to claim 12, wherein the projection is comprised of a tubular member or a coiled member.

16. The guide wire according to claim 12, wherein the projection possesses an outer circumferential surface in which are formed a plurality of recesses.

17. The guide wire according to claim 12, wherein the coating layer possesses a proximal portion terminating at a proximal-most end, the proximal portion possessing a tapering shape that gradually decreases in outside diameter toward the proximal-most end of the coating layer.

18. The guide wire according to claim 12, wherein the resin material includes a urethane resin.

* * * * *